(12) United States Patent
Chen et al.

(10) Patent No.: US 7,172,556 B2
(45) Date of Patent: *Feb. 6, 2007

(54) SPHYGMOMANOMETER

(76) Inventors: Kun-Sung Chen, 9F, No. 78, Sec. 1, Kwang-Fu Rd., San-Chung, Taipei County (TW); Ying-Chao Lin, 9F, No. 78, Sec. 1, Kwang-Fu Rd., San-Chung, Taipei County (TW); Kuo-Hung Huang, 9F, No. 78, Sec. 1, Kwang-Fu Rd., San-Chung, Taipei County (TW); Shin-Lung Du, 9F, No. 78, Sec. 1, Kwang-Fu Rd., San-Chung, Taipei County (TW); Hsing Ouyang, 9F, No. 78, Sec. 1, Kwang-Fu Rd., San-Chung, Taipei County (TW); Yao Ouyang, 9F, No. 78, Sec. 1, Kwang-Fu Rd., San-Chung, Taipei County (TW)

( * ) Notice: Subject to any disclaimer, the term of this patent is extended or adjusted under 35 U.S.C. 154(b) by 200 days.

This patent is subject to a terminal disclaimer.

(21) Appl. No.: 10/982,768

(22) Filed: Nov. 8, 2004

(65) Prior Publication Data
US 2006/0047203 A1  Mar. 2, 2006

(30) Foreign Application Priority Data
Aug. 31, 2004 (TW) .............................. 93213825 U

(51) Int. Cl.
*A61B 5/02* (2006.01)

(52) U.S. Cl. ..................................................... 600/490

(58) Field of Classification Search ................ 600/300, 600/301, 490–503, 481, 483, 485
See application file for complete search history.

(56) References Cited

U.S. PATENT DOCUMENTS

| 4,998,534 | A  | * | 3/1991 | Claxton et al. | ............. | 600/483 |
| 6,353,755 | B1 | * | 3/2002 | Oguma | ....................... | 600/547 |
| 6,447,457 | B1 | * | 9/2002 | Forstner et al. | ............. | 600/485 |
| 6,734,856 | B2 | * | 5/2004 | Ishikawa et al. | ............ | 345/440 |
| 6,905,464 | B2 | * | 6/2005 | Kawanishi et al. | ......... | 600/301 |
| 2002/0002342 | A1 | * | 1/2002 | Iijima et al. | ................ | 600/547 |
| 2003/0094055 | A1 | * | 5/2003 | Sunako et al. | ............. | 73/866.1 |
| 2003/0176796 | A1 | * | 9/2003 | Lin | ............................ | 600/485 |

* cited by examiner

*Primary Examiner*—Charles A Marmor, II
*Assistant Examiner*—Navin Natnithithadha
(74) *Attorney, Agent, or Firm*—Rosenberg, Klein & Lee

(57) ABSTRACT

A sphygmomanometer is disclosed. The sphygmomanometer mainly has plural power buttons and plural memory buttons mounted thereon, and said power buttons and said memory buttons are in a one-on-one manner to communicate with one another. Through pressing one of said power buttons, a measurement value of blood pressure can be directly stored into a correspondingly memory area, and through pressing one of said memory buttons corresponding to that power button, said stored measurement value can be recalled and displayed on said display screen. Therefore, the sphygmomanometer can be provided for more than two users and also can respectively memorize (store) individual measurement value of blood pressure for each user.

8 Claims, 2 Drawing Sheets

SPHYGMOMANOMETER

BACKGROUND OF THE INVENTION

1. Field of the Invention

The present invention is related to a sphygmomanometer, and more particularly to a sphygmomanometer for use by more than two users that also can respectively memorize an individual measurement value of blood pressure for each user.

2. Description of Related Art

On account of diet or the life style, aged people often suffer cardiovascular diseases, and thus may need to measure blood pressure at a set time during daily life. A patient then has to provide the measurement values recorded/stored in the sphygmomanometer to a doctor as reference for diagnosis.

Reference is made to FIG. 1. A conventional sphygmomanometer comprises a main body 11 having an inner unit (including, e.g., circuit component and pneumatic component) mounted inside, a display screen 12 mounted on the main body 11, a power button 13 and a memory button 14 both mounted on the main body 11, a belt 16 for binding the arm of the user and a gas pipe 15 connected between the main body 11 and the belt 16. The pneumatic component inside the main body 11 fills the belt 16 through the gas pipe 15 so as to bind the belt 16 tightly on the arm, the display screen 12 can display all kinds of data and information including the measurement value of blood pressure, the power button 13 is used to turn on the conventional sphygmomanometer 1, and the memory button 14 is used to recall the records of blood pressure stored in a memory for the user's and/or the doctor's reference.

However, in fact, there is often a need for more than one person to use the sphygmomanometer. Therefore, since the conventional sphygmomanometer 1 is designed to conform to only one-person usage, if more than one user wants to use the sphygmomanometer 1, the measurement values recorded will be intermixed and useless to the doctor.

For solving the defect above, it is thought that one memory button 14 can be increased to at least two buttons, so that at least two users can separately store and recall the measurement value thereof. However, this design is still inconvenient because the user has to select the correct memory for blood pressure data storage at each time of measurement. In other words, if A (B) user wants to select A (B) memory area, he has to press the A (B) memory button every time he executes the measurement. For the users who are almost 99% aged people, this design is actually very inconvenient and hard to understand.

SUMMARY OF THE INVENTION

The object of the present invention is to provide a sphygmomanometer for use by multiple users, in which device the measurement values for each user are individually stored, and which is convenient, not troublesome and foolproof.

For achieving the object described above, the present invention provides a sphygmomanometer comprising the following element. A main body has a display screen mounted thereon and an inner unit mounted thereinside. A belt is connected to the inner unit inside the main body through a gas pipe. A plurality of power buttons is mounted on said main body. A plurality of memory buttons is mounted on said main body. The power buttons and memory buttons are identical in number and are correspondingly disposed, and are all electrically connected to said inner unit. By pressing one power button, a measurement value of blood pressure is directly stored into a corresponding memory area of said inner unit, and by pressing the corresponding memory button, the stored measurement value is recalled and displayed on display screen.

BRIEF DESCRIPTION OF THE DRAWINGS

The foregoing aspects and many of the attendant advantages of this invention will be more readily appreciated as the same becomes better understood by reference to the following detailed description, when taken in conjunction with the accompanying drawings, wherein.

DETAILED DESCRIPTION OF PREFERRED EMBODIMENTS

Figure 1:
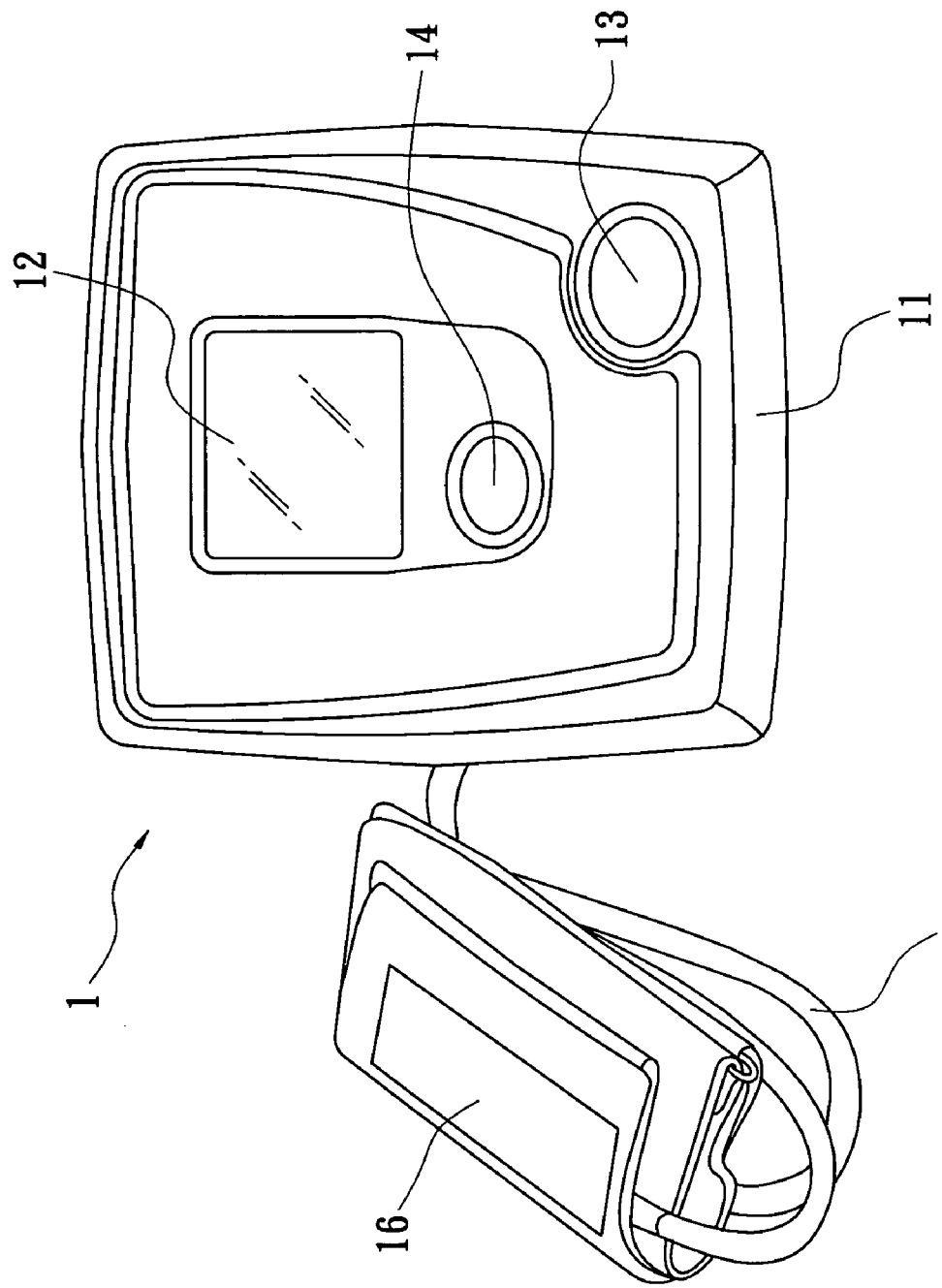
FIG. 1 is a three-dimensional view showing a conventional sphygmomanometer.
Figure 2:
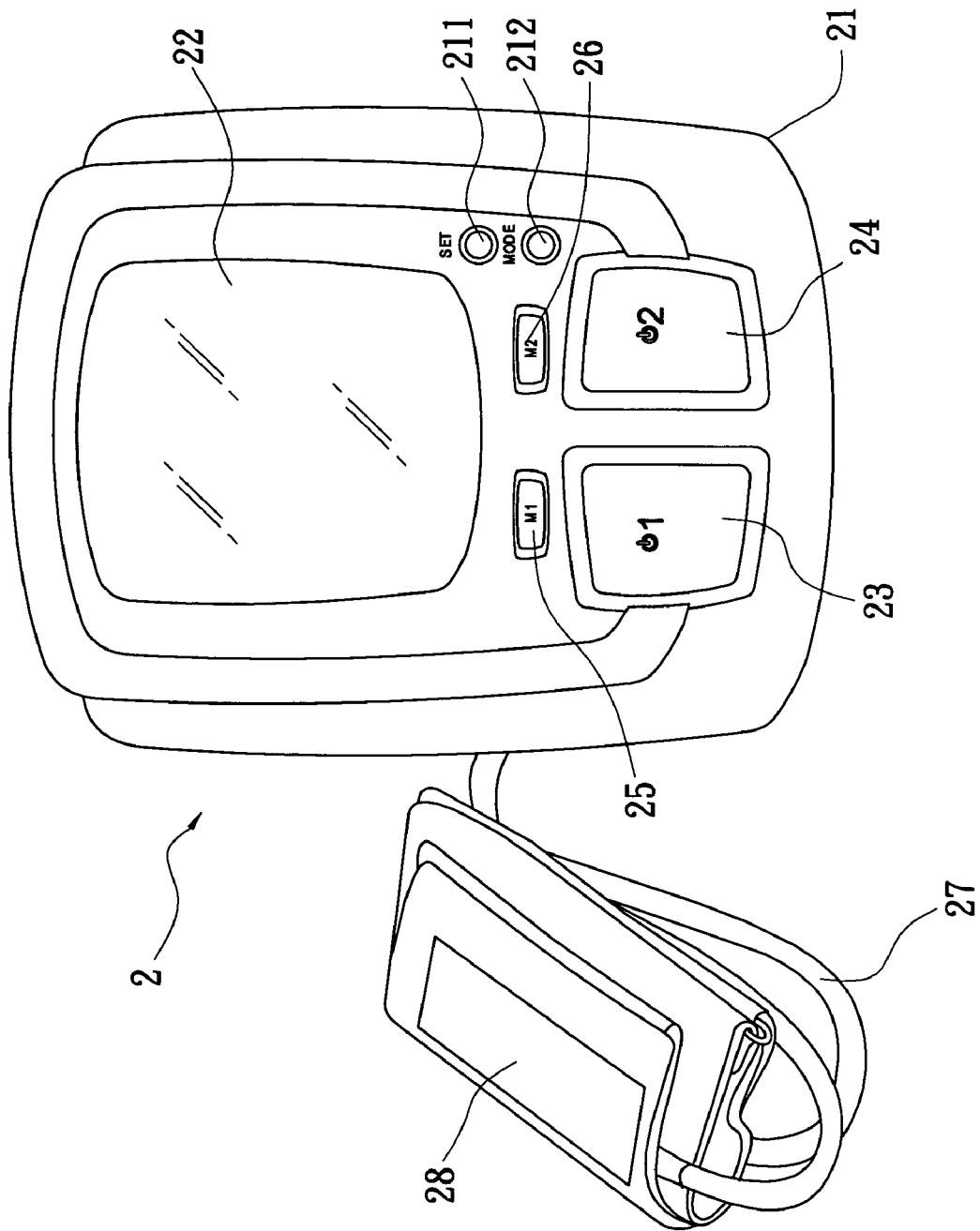
FIG. 2 is a three-dimensional view showing a sphygmomanometer according to the present invention.

Reference is made to FIG. 2. The present invention provides a sphygmomanometer 2 comprising a main body 21, a display screen 22, a first power button 23, a second power button 24 both, a first memory button 25, a second memory button 26, a gas pipe 27, and a belt 28. The display screen 22 can be a LCD display and the main body 21 has an inner unit (not shown) (including circuit component and pneumatic component) mounted inside in substance.

The belt 28 for binding the arm of the user is connected to the inner unit inside the main body 21 through the gas pipe 27 so that the belt 28 can be filled by the pneumatic component of the inner unit.

The first, second power buttons 23, 24 and the first, second memory buttons 25, 26 are all mounted on the main body 21 and also electrically connected with the inner unit. Furthermore, the first, second power buttons 23, 24 and the first, second memory buttons 25, 26 respectively communicate one-on-one with one another.

In addition, each power button can individually turn on or turn off the sphygmomanometer 2.

Therefore, if a first user presses the first button 23 to turn on the sphygmomanometer 2, then the measurement value of blood pressure will not only be displayed on the display screen 22, but also be automatically stored into a first memory area (namely, the memory mounted in the inner unit) without a selection from the user, and if a second user presses the second button 24 to turn on the sphygmomanometer 2, identically, the measurement value of blood pressure will not only be displayed on the display screen 22, but also automatically be stored into a second memory area so that the measurement values are respectively stored into different first and second memory areas without being intermixed and can be provided for the user or the doctor clearly and easily.

When the sphygmomanometer 2 is left unused for a period of time, or the first or second power button 23 or 24 is pressed again after use, the sphygmomanometer 2 is turned off and the first and second memory buttons 25, 26 are standing by. When the first user wants to review his values or show his values to the doctor, he merely presses the first memory button 25 to display the records on the display screen 22. In other words, the second user may display the records on the display screen 22 by correspondingly pressing the second memory button 26. In this manner, a non-confused operation can be achieved.

According to the present invention, for intuitionally informing the aged people that one who presses the first power button 23 should correspondingly press the first memory button 25 for recalling the measurement values, each corresponding memory button is mounted at a position on the main body 21 corresponding to that of the power button.

Furthermore, each power button is designed as a large button, which is far larger than the memory button, so that aged users can easily and clearly recognize which power button is used thereby in the beginning.

Moreover, the sphygmomanometer according to the present invention may further include a setting button 211 and a mode-selecting button 212 mounted on the main body 21, and with the setting button 211 and the mode-selecting button 212 are both electrically connected to the inner unit inside the main body 21.

Certainly, the number of the above-described first, second power buttons 23, 24 and first, second memory buttons 25, 26 is not limited to two and can be more than two so that the sphygmomanometer may be used by more than two users and the measurement value therefor may also be individually stored in one single sphygmomanometer without difficulty.

In accordance with the structure described above, the sphygmomanometer according to the present invention can be provided for two or more than two users to use and to store individually the measurement value thereof so as to prevent intermixing of measurement values, thus providing clear reference to the user or the doctor for observation. Furthermore, the sphygmomanometer according to the present invention is also advantageous in that it is convenient, not troublesome and makes incorrect storage in operation difficultly, so that it is highly suitable for aged people.

As can be seen from the above, the sphygmomanometer according to the present invention, which can exactly solve the defects in the prior arts, is really a product with a highly practical value and also has an increment of efficiency. It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A multi-user sphygmomanometer, comprising:
  a main body having a displaying screen mounted thereon;
  an inner unit mounted inside the main body and including a memory;
  a belt connected to said inner unit through a gas pipe;
  a plurality of power buttons mounted on said main body;
  a plurality of memory buttons mounted on said main body; and
  wherein said power buttons and said memory buttons correspond in number, are correspondingly disposed, and are all electrically connected to said inner unit, each of said corresponding power button and memory button pairs is dedicated to a single one of a plurality of users; and
  wherein, responsive to a single action of pressing one of said power buttons, a measurement value of blood pressure is taken and is directly stored in said memory; and
  wherein, responsive to pressing one of said memory buttons corresponding to said one of said power buttons, said measurement value stored in said memory is recalled and displayed on said display screen.

2. The sphygmomanometer according to claim 1, wherein said power buttons comprise a first and a second power buttons, and said memory buttons comprise a first and a second memory button.

3. The sphygmomanometer according to claim 1, wherein each power button is mounted in a position corresponding to that of each memory button, and each power button and each memory button correspondingly communicate with one another.

4. The sphygmomanometer according to claim 1, wherein each power button is a large button whose size is far larger than that of said memory button.

5. The sphygmomanometer according to claim 1, wherein each power button and each memory button are in a one-on-one manner to communicate with one another.

6. The sphygmomanometer according to claim 1, wherein said main body further comprises a setting button mounted thereon and said setting button is electrically connected to said inner unit.

7. The sphygmomanometer according to claim 1, wherein said main body further comprises a mode-selecting button mounted thereon and said mode-selecting button is electrically connected to said inner unit.

8. The sphygmomanometer according to claim 1, wherein each of said power buttons is employed to individually turn on or turn off said sphygmomanometer.

* * * * *